United States Patent
Song et al.

(10) Patent No.: US 9,612,211 B2
(45) Date of Patent: Apr. 4, 2017

(54) METHODS AND SYSTEMS FOR ENHANCED TIP-TRACKING AND NAVIGATION OF VISUAL INSPECTION DEVICES

(71) Applicant: General Electric Company, Schenectady, NY (US)

(72) Inventors: Guiju Song, Niskayuna, NY (US); Kevin George Harding, Niskayuna, NY (US); Thomas James Batzinger, Burnt Hills, NY (US); Vinod Padmanabhan Kumar, Bangalore Karnataka (IN); Joseph Vincent Pawlowski, Laguna Niguel, CA (US); Kelles Jay Fleming, Barnesville, GA (US)

(73) Assignee: General Electric Company, Niskayuna, NY (US)

( * ) Notice: Subject to any disclaimer, the term of this patent is extended or adjusted under 35 U.S.C. 154(b) by 535 days.

(21) Appl. No.: 13/827,990

(22) Filed: Mar. 14, 2013

(65) Prior Publication Data

US 2014/0278211 A1    Sep. 18, 2014

(51) Int. Cl.
*G01N 21/954* (2006.01)
*G01N 21/88* (2006.01)

(52) U.S. Cl.
CPC ....... *G01N 21/954* (2013.01); *G01N 21/8803* (2013.01)

(58) Field of Classification Search
CPC .................................................. G01N 21/954
(Continued)

(56) References Cited

U.S. PATENT DOCUMENTS 5,096,277 A * 3/1992 Kleinerman ......... G01D 5/3538
374/131
5,699,444 A 12/1997 Palm
(Continued)

OTHER PUBLICATIONS

Martin et al., "Real Time Tracking of Borescope Tip Pose", Undated, 12 pages, Department of Computer Science, Rensselaer Polytechnic Institute, Troy, NY, USA.
(Continued)

*Primary Examiner* — Gregory J Toatley
*Assistant Examiner* — Felix Suarez
(74) *Attorney, Agent, or Firm* — Ann M. Agosti (57) ABSTRACT

A computer-implemented system for enhanced tip-tracking and navigation of visual inspection devices includes a visual inspection device. The system further includes a plurality of spatially sensitive fibers. The system includes a computing device. The computing device includes a memory device and a processor. The system includes a storage device. The storage device includes an engineering model representing the physical asset. The computing device is configured receive an insertion location from the visual inspection device. The computing device is configured to receive fiber information associated with the visual inspection device. The computing device is configured to determine the real-time location of the visual inspection device using the fiber information. The computing device is configured to identify the real-time location of the visual inspection device with respect to the engineering model. The computing device is configured to navigate the visual inspection device from a first location to a second location.

20 Claims, 4 Drawing Sheets

(58) Field of Classification Search
USPC ............ 702/38, 67, 115, 150, 164; 356/237;
320/101
See application file for complete search history.

(56) References Cited

U.S. PATENT DOCUMENTS

| | | | |
|---|---|---|---|
| 5,774,212 A * | 6/1998 | Corby, Jr. ................... | 356/237.2 |
| 5,850,469 A | 12/1998 | Martin et al. | |
| 6,985,620 B2 | 1/2006 | Sawhney et al. | |
| 6,992,315 B2 | 1/2006 | Twerdochlib | |
| 7,520,176 B1 | 4/2009 | Ko et al. | |
| 7,715,994 B1 | 5/2010 | Richards et al. | |
| 7,720,322 B2 | 5/2010 | Prisco | |
| 8,125,529 B2 | 2/2012 | Skoskiewicz et al. | |
| 8,171,809 B2 | 5/2012 | Fritz | |
| 8,184,152 B2 | 5/2012 | Pryor et al. | |
| 8,664,911 B1 * | 3/2014 | Oakenfull ..................... | 320/101 |
| 2004/0066273 A1 * | 4/2004 | Cortina et al. ................ | 340/5.1 |
| 2009/0154293 A1 | 6/2009 | Sengupta et al. | |
| 2010/0140936 A1 | 6/2010 | Benito et al. | |
| 2010/0275574 A1 | 11/2010 | Salunkhe | |
| 2010/0277719 A1 * | 11/2010 | Chen ..................... | G08B 13/186 356/73.1 |
| 2012/0224049 A1 | 9/2012 | Cox | |

OTHER PUBLICATIONS

Vembar et al., "A Haptic Virtual Borescope for Visual Engine Inspection Training", Mar. 8, 2008, pp. 19-26, IEEE Symposium on 3D User Interfaces.
Trimble, "Locating Underground Pipe Defects Across Canada".
Vembar et al., "Visuohaptic Borescope Inspection Simulation Training: Modeling Multi-Point Collision Detection/Response and Evaluating Skills Transfer".
Brant et al., "Plataformarobotiz Ada Tipoboroscopio Para Inspecao Visual", Sep. 12-16, 2010, XVIII Congresso Brasileiro de Automatica, Bonito-MS.
Gramopadhye et al., "The Application of Advanced Technology to Education: The Aviation Inspection Example", Jun. 25-27, 2012, ACTA Press-Computers and Advanced Technology in Education—2012, Napoli, Italy.

* cited by examiner

METHODS AND SYSTEMS FOR ENHANCED TIP-TRACKING AND NAVIGATION OF VISUAL INSPECTION DEVICES

BACKGROUND

The disclosure relates generally to a computer-implemented system for enhanced tip-tracking and navigation of visual inspection devices.

Known methods of visual inspection of physical assets include the use of optical devices inserted within such physical assets, wherein the entrance to the physical asset typically has limited or no human access. Such known methods provide benefits by allowing for rapid visual analysis of complex physical assets that may be inaccessible to human technicians without disassembly or other servicing. In some such known cases, disassembly or servicing of complex physical assets may take hours to perform. During such disassembly or servicing, many such complex physical assets must be rendered temporarily inoperable, resulting in costly asset downtime. Therefore, known methods of visual inspection rapidly expedite analysis of internal conditions of complex physical assets and reduce downtime that may be caused by disassembly or servicing.

Known methods and systems of visual inspection of physical assets generally involve sending visual data to human technicians capable of diagnosing conditions of the complex physical assets. Human technicians may review such visual data using monitors, computers, or other displays.

Known problems of visual inspection of physical assets using optical devices include proper identification of the location and orientation of the visual inspection device within the physical asset. In large and/or complex systems, the visual inspection device may move significant distances and rotate or otherwise change position. Efficient analysis of visual inspection data requires understanding the location of the visual inspection device which may not always be possible. In addition, the data analysis is dependent upon the experience and subjective nature of the operated and tends to result in inconsistent diagnosis and recommendations.

BRIEF DESCRIPTION

In one aspect, a computer-implemented system for enhanced tip-tracking and navigation of visual inspection devices is provided. The system includes a visual inspection device capable of capturing data regarding physical characteristics of the physical asset. The system also includes an enclosure at least partially containing the visual inspection device. The system further includes a plurality of spatially sensitive fibers at least partly encased in the enclosure. The system additionally includes a computing device. The computing device includes a memory device and a processor coupled to the memory device. Moreover, the system includes a storage device coupled to the computing device. The storage device includes an engineering model substantially representing the physical asset. The computing device is configured receive an insertion location from the visual inspection device. Insertion location substantially represents a point where the visual inspection device is inserted into the physical asset. The computing device is also configured to receive fiber information associated with the visual inspection device from the plurality of spatially sensitive fibers. The computing device is further configured to determine the real-time location of the visual inspection device using the fiber information. The computing device is additionally configured to identify the real-time location of the visual inspection device with respect to the engineering model. The computing device is moreover configured to navigate the visual inspection device from a first location to a second location within the physical asset.

In a further aspect, a computer-based method for enhanced tip-tracking and navigation of visual inspection devices is provided. The method is performed by a computing device. The computing device includes a processor. The computing device also includes a memory device coupled to the processor. The computing device also includes a storage device coupled to the memory device and also coupled to the processor. The storage device includes an engineering model substantially representing the physical asset. The method includes receiving an insertion location at the computing device from the visual inspection device. The insertion location substantially represents a point where the visual inspection device is inserted into the physical asset. The method also includes transmitting fiber information to the computing device from a plurality of spatially sensitive fibers at least partly encased in an enclosure at least partially containing the visual inspection device. The method further includes determining the real-time location of the visual inspection device using the fiber information. The method additionally includes identifying the real-time location of the visual inspection device with respect to the engineering model. The method moreover includes navigating the visual inspection device from a first location to a second location within the physical asset.

In another aspect, a computer for enhanced tip-tracking and navigation of visual inspection devices is provided. The computer includes a storage device. The storage device includes an engineering model substantially representing the physical asset. The computer also includes a processor coupled to the storage device. The computer further includes a memory device coupled to the processor and also coupled to the storage device. The memory device includes processor-executable instructions. When executed by the processor, processor-executable instructions cause the computer to receive an insertion location from the visual inspection device. The insertion location substantially represents a point where the visual inspection device is inserted into the physical asset. When executed by the processor, processor-executable instructions also cause the computer to receive fiber information associated with the visual inspection device from a plurality of spatially sensitive fibers. When executed by the processor, processor-executable instructions further cause the computer to determine the real-time location of the visual inspection device using the fiber information. When executed by the processor, processor-executable instructions further additionally the computer to identify the real-time location of the visual inspection device with respect to the engineering model. When executed by the processor, processor-executable instructions moreover cause the computer to navigate the visual inspection device from a first location to a second location within the physical asset.

DRAWINGS

These and other features, aspects, and advantages will become better understood when the following detailed description is read with reference to the accompanying drawings in which like characters represent like parts throughout the drawings, wherein.

Unless otherwise indicated, the drawings provided herein are meant to illustrate key inventive features of the invention. These key inventive features are believed to be applicable in a wide variety of systems comprising one or more embodiments of the invention. As such, the drawings are not meant to include all conventional features known by those of ordinary skill in the art to be required for the practice of the invention.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the terms "software" and "firmware" are interchangeable, and include any computer program stored in memory for execution by devices that include, without limitation, mobile devices, clusters, personal computers, workstations, clients, and servers.

As used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein.

As used herein, the term "visual inspection device" and related terms, e.g., "visual inspection devices," refers to any optical device capable of being inserted into a physical asset, moving within the physical asset, capturing visual data regarding the physical asset, and transmitting the visual data. Such visual inspection devices may include, without limitation, borescopes, fiberscopes, video borescopes, rigid borescopes, or any digital camera capable of being inserted and maneuvered within a physical asset. Also, as used herein, enhanced tip-tracking and navigation is provided to visual inspection devices.

As used herein, the term "physical asset" and related terms, e.g., "assets," refers to any physical object that may be inspected using a visual inspection device. Such assets may include, without limitation, gas turbines, steam turbines, aircraft engines, diesel engines, automotive engines, truck engines, pressure vessels, and any simple or complex machinery that may be penetrated by a visual inspection device. Also, as used herein, physical assets are visually inspected with by visual inspection devices using enhanced tip-tracking and navigation.

As used herein, the term "engineering model" and related terms, e.g., "engineering model data," refers to any graphical model that substantially represents a physical asset. Such engineering models may include, without limitation, computer-aided drawings (CAD), computer-aided industrial design, photo realistic renderings, and any other model that substantially represents a physical asset and can be used to depict a typical physical asset. Also, as used herein, engineering models are used to identify a real-time location of the visual inspection device.

As used herein, the term "thermal drift" and related terms, e.g., "thermal drift effects," refers to a reduction in the accuracy of sensor data caused by temperature fluctuations in or near the visual inspection device, the spatially sensitive fibers, or the enclosure. Also, as used herein, thermal drift may be compensated for by using a supplemental spatially sensitive fiber.

As used herein, the term "spatially sensitive fibers" and related terms, e.g., "fiber sensors," refers to a sensor that uses optical fiber either as a sensing element and/or as a means of relaying signals from a remote sensor to the electronics that process the signals. Spatially sensitive fibers may include, without limitation, fiber optic sensors, long-period fiber grating optical fibers, or any other fibers that can be wavelength multiplexed to determine bending measurements. Also, as used herein, spatially sensitive fibers transmit fiber information to the computing device to determine the real-time location of the visual inspection device.

As used herein, the term "fiber information" and related terms refers to data transmitted by spatially sensitive fibers that may be used to allow the computing device to determine the location of the visual inspection device. Fiber information may include, without limitation, acceleration data, tension data, torsion data, light levels, attenuation band, bending data, and any other data that can be relayed by spatially sensitive fibers to determine the location of the visual inspection device.

As used herein, the term "breadcrumb navigation" and related terms, e.g., "GPS-like navigation," refers to methods that allow the tracking of a physical object based upon an initial reference point and data referring to component motion of the physical asset. In other words, breadcrumb navigation involves applying an initial location for a physical object to motion data of the object (e.g., a vector) to identify a new location of the physical object. Breadcrumb navigation can further compound motion data to determine relative shifts from each motion data. Applying such compounded motion data to a known original location, breadcrumb navigation can be used to determine a location of the physical object based upon multiple motion data values. As used herein, breadcrumb navigation facilitates converting an initial position of the physical asset and fiber information into a real-time location for the visual inspection device.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Figure 1:
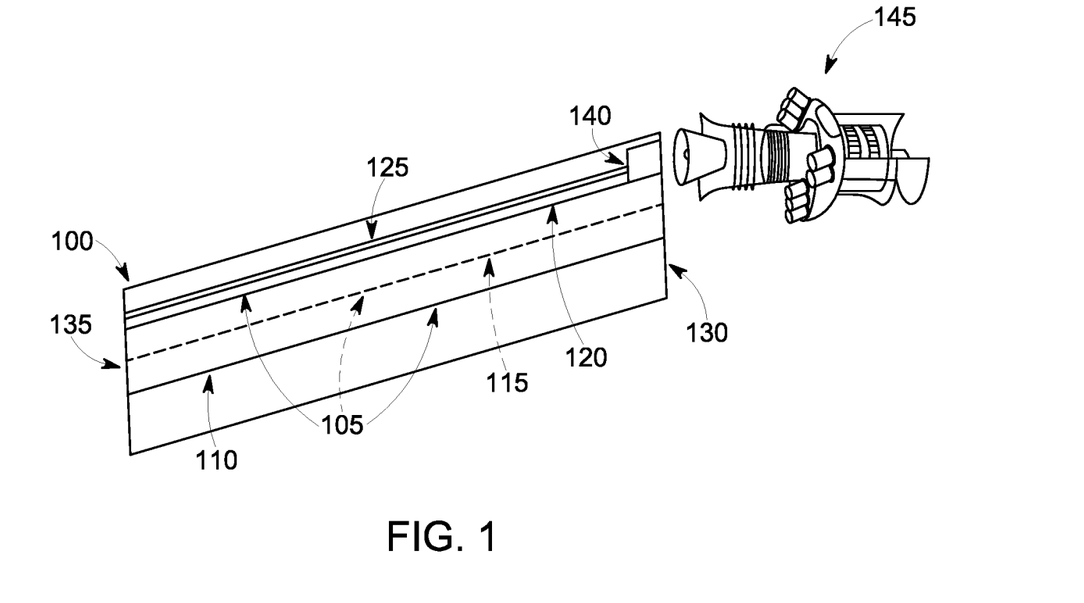
FIG. 1 is a schematic view of an exemplary high-level view of an enclosure that may be used with a computer-implemented system for enhanced tip-tracking and navigation of visual inspection devices.

FIG. 1 is a schematic view of an exemplary high-level view of an enclosure 100 that may be used with a computer-implemented system for enhanced tip-tracking and navigation of visual inspection devices. Enclosure 100 is a physical housing which at least partially encases a plurality of spatially sensitive fibers 105, a visual data capturing device 140, and an optical relay fiber 125. In an exemplary embodiment, enclosure 100 is a plastic housing. In alternative embodiments, enclosure 100 may be made of a suitable material which can at least partially encase spatially sensitive fibers 105, visual data capturing device 140, and optical fiber relay 125. In the exemplary embodiment, spatially sensitive fibers 105 are fiber optic fibers. Also, in the exemplary embodiment, visual data capturing device 140 is a miniature video camera. In alternative embodiments, visual data capturing device 140 may be any device capable of capturing visual information and transmitting such visual information along optical relay fiber 125.

In operation enclosure 100 may be inserted at a tip (i.e., a distal end) 130 into a physical asset 145 to inspect physical asset 145 using enhanced tip-tracking and navigation. Tip 130 is therefore representative of the location from which images of physical asset 145 are taken. Enclosure 100 may be controlled for insertion by a user (not shown in FIG. 1) using a handset (not shown in FIG. 1) or other computing device (not shown in FIG. 1). At a proximal end 135, enclosure 100 continues (not shown) towards the handset or computing device while maintaining the same composition and structure.

Spatially sensitive fibers 105 include a first spatially sensitive fiber 110 and a second spatially sensitive fiber 120. Spatially sensitive fibers 105 are capable of capturing and transmitting fiber information (not shown in FIG. 1) which can be used to determine the location and orientation of tip 130 of enclosure 100. In at least some embodiments, spatially sensitive fibers 105 includes a supplemental spatially sensitive fiber 115 which can be used to provide fiber information that can compensate for thermal drift in enclosure 100. Spatially sensitive fibers 105 terminate at tip 130 adjacent to visual data capturing device 140.

Figure 2:
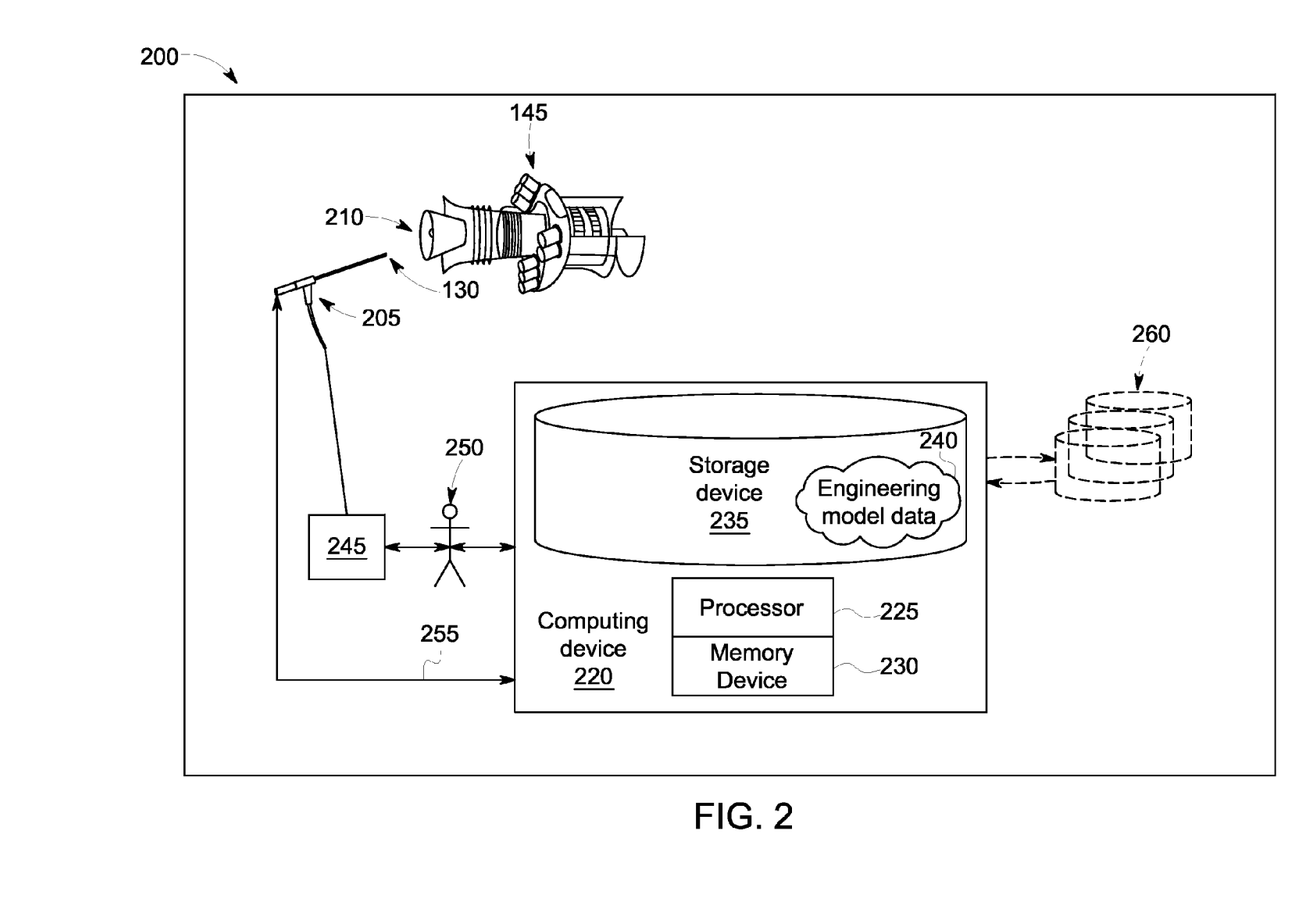
FIG. 2 is a schematic view of an exemplary high-level computer-implemented system for enhanced tip-tracking and navigation of visual inspection devices.

FIG. 2 is a schematic view of an exemplary high-level computer-implemented system 200 for enhanced tip-tracking and navigation of visual inspection devices 205. Visual inspection device 205 is representative of a device for visual inspection including enclosure 100 (shown in FIG. 1) to capture and transmit visual data and fiber information 255. Visual inspection device 205 is used to inspect a physical asset 145. In the exemplary embodiment, physical asset 145 is a steam turbine. In alternative embodiments, physical asset 145 may be any physical object including, without limitation, gas turbines, aircraft engines, diesel engines, automotive engines, truck engines, pressure vessels, piping systems, generators, reduction gears, transformers, and any simple or complex machinery. In the exemplary embodiment, visual inspection device 205 is a borescope. In alternative embodiments, visual inspection device 205 may include, without limitation, fiberscopes, video borescopes, rigid borescopes, or any digital camera device capable of being inserted and maneuvered within physical asset 145. In the exemplary embodiment, visual inspection device 205 is associated with handset 245 which may be used to navigate and control the movement of visual inspection device 205. Handset 245 is representative of a computing device capable of such navigation and control. In other embodiments, visual inspection device 205 may be controlled by other computing devices such as computing device 220. Visual inspection device 205 is also capable of transmitting fiber information 255.

Computer-implemented system 200 also includes computing device 220. Computing device 220 includes at least one processor 225 and a memory device 230. Processor 225 and memory device 230 are communicatively coupled to one another. In the exemplary embodiment, computing device 220 includes one processor 225 and one memory device 230. In alternative embodiments, computing device 220 may include a plurality of processors 225 and/or a plurality of memory devices 230.

Computing device 220 in one example also includes a storage device 235. The storage device 235 is coupled to processor 225 and also coupled to the memory device 230. In the exemplary embodiment, storage device 235 is a hard disk drive. In alternative embodiments, storage device 235 may be any storage device including, without limitation, optical storage devices, magnetic storage devices, network storage devices, flash storage devices, mass storage devices, and any other storage device capable of storing data for computer-implemented system 200. In at least some embodiments, computing device 220 is associated with external storage 260. In such embodiments, external storage 260 stores data that may be written to storage device 235 or used directly by computing device 220.

In the exemplary embodiment, storage device 235 includes engineering model data 240. Engineering model data 240 represents data of engineering designs of physical asset 145. In the exemplary embodiment, engineering model data 240 includes computer-aided drawings (CAD). In alternative embodiments, engineering model data 240 may include, without limitation, computer-aided industrial design, photo realistic renderings, and any other model that substantially represents a physical asset and can be used to depict typical physical asset 145.

In operation, tip 130 of visual inspection device 205 is inserted into asset opening 210 of physical asset 145. Once inserted, visual inspection device 205 transmits visual data (not shown) representative of images of the inside of physical asset 145 to handset 245 or computing device 220. Visual inspection device 205 is inserted and controlled by user 250.

In the exemplary embodiment, user 250 controls visual inspection device 205 with handset 245. In alternative embodiments, user 250 controls visual inspection device with other computing devices including computing device 220. Visual inspection device 205 transmits fiber information 255 to computing device 220. Computing device 220 receives fiber information 255 from visual inspection device 205. Fiber information 255 represents data that may be used to determine relative location (i.e., relative to asset opening 210) of tip 130 of visual inspection device 205. In the exemplary embodiment, fiber information 255 includes bending measurements from multiplexed fiber sensors. In alternative embodiments, fiber information 255 may include fiber tension or torsion as sensed by the fiber, light levels and light loss, signal loss due to decreased internal reflections caused by fiber bending, changes in signal bandwidth, wavelength shifts, depth change of attenuation bands, splitting of attenuation bands, and optical effects in the fiber. Tension or torsion data may be used to determine the bending of spatially sensitive fibers 105 (shown in FIG. 1) and therefore the bending of enclosure 100 and therefore may (when used with breadcrumb navigation) be used to determine a relative location of tip 130. Light levels may be used to determine that a fiber from spatially sensitive fibers 105 has light loss. By calculating the light loss at each multiplexed sensor, bending radius of the fiber may be determined. By combining the bending radius at each multiplexed sensor, a relative location of tip 130 may similarly be determined. Wavelength shifts, depth change of attenuation bands, and splitting of attenuation bands may be used to measure a relative bending change and determine a three-dimensional change in position of fiber. In all embodiments, such fiber information 255 can be used to determine a relative movement along multiplexed fiber sensors. By collecting such movements and using breadcrumb navigation along with a known location of insertion (i.e., asset opening 210) of visual inspection device 205, an absolute location of tip 130 can be determined.

Processor 225 cascades fiber information 255 into a vector (not shown) containing values at each length of the enclosure for shape and directional information. Cascading fiber information 255 represents aggregating individual fiber information 255 along the length of spatially sensitive fibers 105 so that overall bending and motion of spatially sensitive fibers 105 (and therefore enclosure 100 and tip 130) can be determined. Processor 225 also applies an algorithm to determine the path of tip 130 of visual inspection device 205 using cascaded fiber information 255 and location of asset opening 210. In the exemplary embodiment, the algorithm includes navigation methods to determine a real-time location (not shown) for tip 130 of visual inspection device 205 based upon fiber information 255.

Further, processor 225 retrieves engineering model data 240 from storage device 235 and applies fiber information 255 to determine a real-time location (not shown) of visual inspection device 205 with respect to engineering model data 240.

Additionally, by applying known location information and engineering model data 240, processor 225 navigates tip 130 of visual inspection device 205 from a first location within physical asset 145 to a second location in physical asset 145. In the exemplary embodiment, navigating tip 130 of visual inspection device 205 requires processor 225 to control visual inspection device 205 via a communication link. In alternative embodiments, navigating tip 130 of visual inspection device 205 may involve presenting information to user 250 who controls navigation of visual inspection device 205 with handset 245. In other embodiments, user 250 may specify at computing device 220, a second location to navigate tip 130 towards using a user input interface (not shown in FIG. 2).

Figure 3:
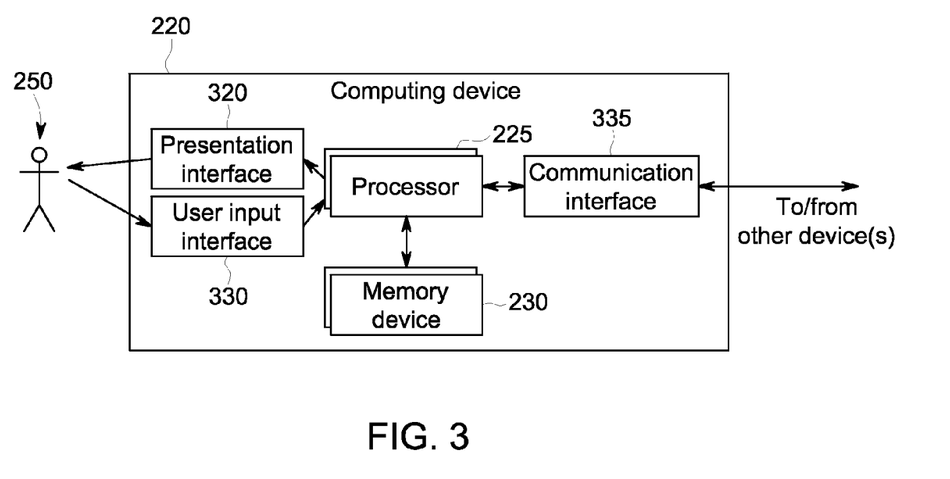
FIG. 3 is a block diagram of an exemplary computing device that may be used with the computer-implemented system shown in FIG. 2.

FIG. 3 is a block diagram of exemplary computing device 220 that may be used with computer-implemented system 200 (shown in FIG. 2). Computing device 220 includes a memory device 230 and a processor 225 operatively coupled to memory device 230 for executing instructions. In the exemplary embodiment, computing device 220 includes a single processor 225 and a single memory device 230. In alternative embodiments, computing device 220 may include a plurality of processors 225 and/or a plurality of memory devices 230. In some embodiments, executable instructions are stored in memory device 230. Computing device 220 is configurable to perform one or more operations described herein by programming processor 225. For example, processor 225 may be programmed by encoding an operation as one or more executable instructions and providing the executable instructions in memory device 230.

In the exemplary embodiment, memory device 230 is one or more devices that enable storage and retrieval of information such as executable instructions and/or other data. Memory device 230 may include one or more tangible, non-transitory computer-readable media, such as, without limitation, random access memory (RAM), dynamic random access memory (DRAM), static random access memory (SRAM), a solid state disk, a hard disk, read-only memory (ROM), erasable programmable ROM (EPROM), electrically erasable programmable ROM (EEPROM), and/or non-volatile RAM (NVRAM) memory. The above memory types are exemplary only, and are thus not limiting as to the types of memory usable for storage of a computer program.

Memory device 230 may be configured to store operational data including, without limitation, fiber information 255 (shown in FIG. 2), and/or any other type of data. In some embodiments, processor 225 removes or "purges" data from memory device 230 based on the age of the data. For example, processor 225 may overwrite previously recorded and stored data associated with a subsequent time and/or event. In addition, or alternatively, processor 225 may remove data that exceeds a predetermined time interval. Also, memory device 230 includes, without limitation, sufficient data, algorithms, and commands to facilitate operation of computer-implemented system 200.

In some embodiments, computing device 220 includes a user input interface 330. In the exemplary embodiment, user input interface 330 is coupled to processor 225 and receives input from user 250. User input interface 330 may include, without limitation, a keyboard, a pointing device, a mouse, a stylus, a touch sensitive panel, including, e.g., without limitation, a touch pad or a touch screen, and/or an audio input interface, including, e.g., without limitation, a microphone. A single component, such as a touch screen, may function as both a display device of presentation interface 320 and user input interface 330.

A communication interface 335 is coupled to processor 225 and is configured to be coupled in communication with one or more other devices, such as a sensor or another computing device 220, and to perform input and output operations with respect to such devices. For example, communication interface 335 may include, without limitation, a wired network adapter, a wireless network adapter, a mobile telecommunications adapter, a serial communication adapter, and/or a parallel communication adapter. Communication interface 335 may receive data from and/or transmit data to one or more remote devices. For example, a communication interface 335 of one computing device 220 may transmit an alarm to communication interface 335 of another computing device 220. Communications interface 335 facilitates machine-to-machine communications, i.e., acts as a machine-to-machine interface.

Presentation interface 320 and/or communication interface 335 are both capable of providing information suitable for use with the methods described herein, e.g., to user 250 or another device. Accordingly, presentation interface 320 and communication interface 335 may be referred to as output devices. Similarly, user input interface 330 and communication interface 335 are capable of receiving information suitable for use with the methods described herein and may be referred to as input devices.

In the exemplary embodiment, user 250 may use computing device 220 by receiving information on fiber information 255, the real-time location (not shown) of tip 130 (shown in FIG. 2) of visual inspection device 205 (shown in FIG. 2), and the real-time location (not shown) of tip 130 of visual inspection device 205 with respect to engineering model data 240 (shown in FIG. 2). User 250 may act on the information presented and use computing device 220 to update or correct the location of visual inspection device 205, to navigate tip 130 of visual inspection device 205 to a second location, or to continue inspection of physical asset 145. User 250 may initiate such an action via user input interface 330 which processes the user command at processor 225 and uses communication interface 335 to communicate with other devices.

In the exemplary embodiment, computing device 220 is an exemplary embodiment of computing device 220. In at least some other embodiments, computing device 220 is also an exemplary embodiment of handset 245 (shown in FIG. 2), or other devices (not shown) used for enhanced tip-tracking and navigation of visual inspection devices 205. In most embodiments, computing device 220 at least illustrates the primary design of such other devices.

Figure 4:
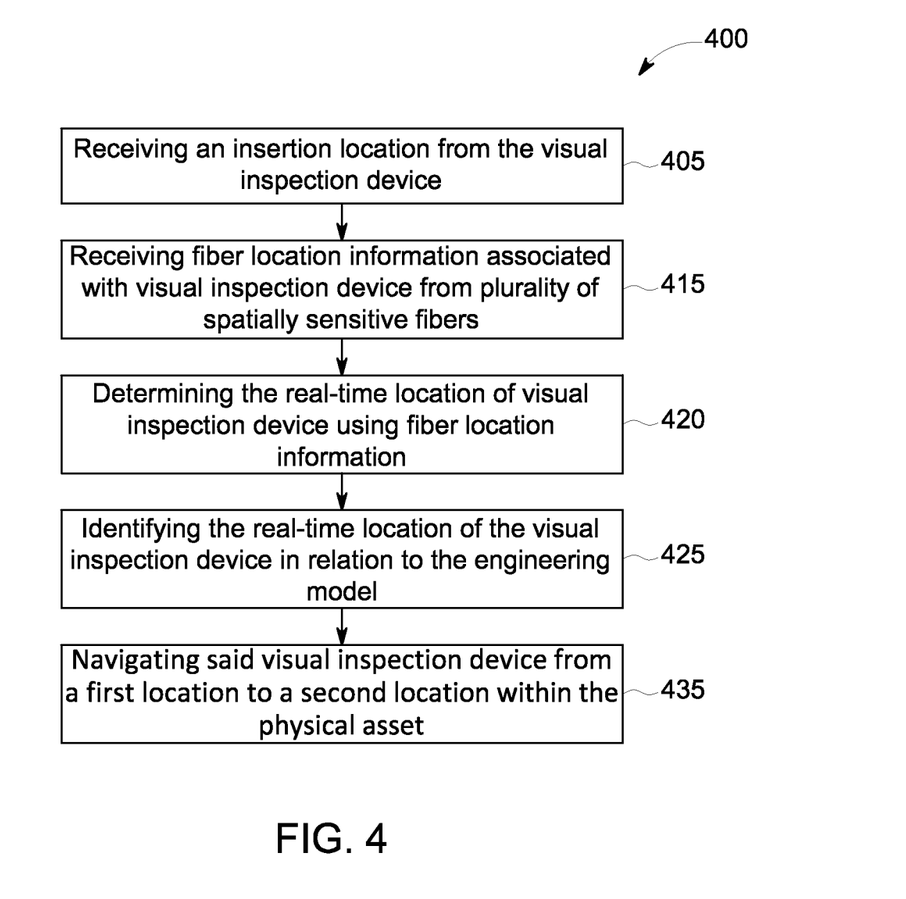
FIG. 4 is a simplified flow chart of the overall method for enhanced tip-tracking and navigation of visual inspection devices using the computer-implemented system shown in FIG. 2.

FIG. 4 is a simplified flow chart of an overall method 400 for enhanced tip-tracking and navigation of visual inspection devices 205 using computer-implemented system 200 (both shown in FIG. 2). Method 400 is executed at processor 225 (shown in FIG. 2) in computing device 220 (shown in FIG. 2). Computing device 220 receives 405 a insertion location from visual inspection device 205 (shown in FIG. 2). Receiving 405 a insertion location represents receiving a reference to asset opening 210 (shown in FIG. 2) with respect to engineering model data 240 (shown in FIG. 2). Insertion location can be used in conjunction with fiber information 255 to determine an absolute location of tip 130 (shown in FIG. 2) with respect to engineering model data 240.

Computing device 220 receives 415 fiber information associated with visual inspection device from plurality of spatially sensitive fibers 105 (shown in FIG. 1). Receiving 415 fiber information represents receiving fiber information 255 (shown in FIG. 2) from spatially sensitive fibers 105 located within enclosure 100 (shown in FIG. 1). As described above, fiber information 255 may include, without limitation, fiber tension or torsion as sensed by the fiber, light levels and light loss, signal loss due to decreased internal reflections caused by fiber bending, changes in signal bandwidth, wavelength shifts, depth change of attenuation bands, splitting of attenuation bands, and optical effects in the fiber. Fiber information 255 is generally reflective of data that can be used to determine shape and direction of spatially sensitive fibers 105.

Computing device 220 also determines 420 the real-time location of visual inspection device using fiber information. Determining 420 the real-time location of visual inspection device represents cascading fiber information 255 and applying at least one algorithm to determine the location of visual inspection device 205. As described above, cascading represents aggregating individual fiber information 255 along the length of spatially sensitive fibers 105 so that overall bending and motion of spatially sensitive fibers 105 (and therefore enclosure 100 and tip 130) can be determined. The algorithm then determines the path of tip 130 of visual inspection device 205 using cascaded fiber information 255 and location of asset opening 210. The algorithm applies breadcrumb navigation so that it that can determine a real-time location for visual inspection device 205 based upon cascaded fiber information 255 and known location of insertion of tip 130 into asset opening 210.

Computing device 220 further identifies 425 the real-time location of visual inspection device in relation to the engineering model. Identifying 425 the real-time location of visual inspection device represents applying the determined 420 real-time location of visual inspection device 205 to engineering model data 240. Applying real-time location of visual inspection device 205 to engineering model data 240 includes using mapping algorithms to find the location of visual inspection device 205 based upon the received 405 point of entry (i.e. asset opening 210) of tip 130 (shown in FIG. 2) of visual inspection device 205, determined 420 real-time location, and engineering model data 240. In other words, computing device 220 determines point of entry of tip 130 on engineering model data 240 and uses determined 420 real-time location to identify the relative location of tip 130 on engineering model data 240.

Computing device 220 additionally navigates 435 the visual inspection device from a first location to a second location within the physical asset. Navigating 435 visual inspection device 205 represents calculating a route for tip 130 to travel within physical asset 145 based upon engineering model data 240, the known first location (i.e., determined 420 real-time location and identified 425 real-time location in relation to engineering model data 240), and an input second location. In the exemplary embodiment, the second location is determined by user 250 (shown in FIG. 2) at handset 245 (shown in FIG. 2) or user input interface 330 (shown in FIG. 3) of computing device 220.

The computer-implemented systems and methods as described herein provide an efficient approach for enhanced tip-tracking and navigation of visual inspection devices. The embodiments described herein reduce the cycle time for technicians to complete visual inspections and enhanced visual inspections. Also, the methods and systems described herein increase the maintainability of physical assets by better inspection and analysis. Further, the methods and systems described herein improve asset management by improving anomaly analysis and detection through improved traceable inspection. Additionally, the methods and systems described herein will reduce the operational, logistical, and financial costs associated with the inspection of physical assets through more efficient inspections and analysis.

An exemplary technical effect of the methods and computer-implemented systems described herein includes at least one of (a) reduce costs of visual inspections by reducing navigation time; (b) reducing error rates in visual inspections with more accurate navigation; (c) improved physical asset maintenance due to more precise inspections;

and (d) increased ability to visually inspect physical assets due to reduced navigation time.

Exemplary embodiments of computer-implemented systems implementing enhanced tip-tracking and navigation of visual inspection devices are described above in detail. The computer-implemented systems and methods of operating such systems are not limited to the specific embodiments described herein, but rather, components of systems and/or steps of the methods may be utilized independently and separately from other components and/or steps described herein. For example, the methods may also be used in combination with other enterprise systems and methods, and are not limited to practice with only visual inspection devices systems and methods as described herein. Rather, the exemplary embodiment can be implemented and utilized in connection with many other enterprise applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented system for enhanced tip-tracking and navigation of visual inspection devices, said system comprising:
    a visual inspection device for capturing data regarding physical characteristics of a physical asset, comprising:
        an enclosure having a tip at one end for inserting into an opening of the physical asset;
        a visual data capturing device at least partially encased in an enclosure and located at a tip of said enclosure;
        a plurality of spatially sensitive fibers at least partly encased in said enclosure and terminating at said tip adjacent said visual data capturing device; and
    a computing device operatively coupled to said visual inspection device, said computing device including a memory device, a processor coupled to said memory device, and a storage device including an engineering model data substantially representing the physical asset, said computing device configured to:
        receive an insertion location from said visual inspection device, wherein an insertion location substantially represents a reference to a point of entry where said tip of said visual inspection device is inserted into the opening of the physical asset;
        receive fiber information captured and transmitted from said plurality of spatially sensitive fibers;
        determine bending and motion information about said plurality of spatially sensitive fibers from said fiber information;
        determine the real-time location of said tip of said visual inspection device using the insertion location and the bending and motion information;
        identify the real-time location of said tip of said visual inspection device with respect to said engineering model data; and
        navigate said tip of said visual inspection device from a first location to a second location within the physical asset.

2. A computer-implemented system in accordance with claim 1, wherein said plurality of spatially sensitive fibers comprise:
    a first spatially sensitive fiber to determine the vertical orientation of said visual inspection device; and
    a second spatially sensitive fiber to determine the horizontal orientation of said visual inspection device,
    wherein the fiber information comprises fiber tension information, fiber torsion information, light level information, signal loss information, signal bandwidth information, wavelength information, or attenuation information.

3. A computer-implemented system in accordance with claim 2 further comprising a supplemental spatially sensitive fiber to compensate for error in the event of thermal drift effects within said plurality of spatially sensitive fibers.

4. A computer-implemented system in accordance with claim 1, wherein said computing device is further configured to:
    cascade said fiber information into a vector containing values at each length of said enclosure for shape and direction information associated with said plurality of spatially sensitive fibers; and
    determine the path of said visual inspection device using said vector and at least one algorithm.

5. A computer-implemented system in accordance with claim 1, wherein said computing device is configured to navigate said visual inspection device from a first location to a second location within the physical asset, said computing device is further configured to:
    receive a second location from a computing device associated with said visual inspection device; and
    transmit a navigation route to the computing device associated with said visual inspection device.

6. A computer-implemented system in accordance with claim 1, wherein said visual inspection device is a borescope.

7. A computer-implemented system in accordance with claim 1, wherein said at least two spatially sensitive fibers comprise wavelength multiplexed fiber sensors for bending measurement at multiple locations.

8. A computer-based method for enhanced tip-tracking and navigation of visual inspection devices, wherein said method is performed by a visual inspection device for capturing data regarding physical characteristics of a physical assert, the visual inspection device including an enclosure having a tip at one end for inserting into an opening of the physical asset, a visual data capturing device at least partially encased in an enclosure and located at a tip of said enclosure, a plurality of spatially sensitive fibers at least partly encased in said enclosure and terminating at said tip adjacent said visual data capturing device, and an optical relay fiber at least partially encased in said enclosure for transmitting visual information from said visual data capturing device; and a computing device including a processor, a memory device coupled to the processor, and a storage device coupled to the memory device and to the processor, wherein the storage device includes an engineering model data substantially representing the physical asset, said method comprising:

receiving an insertion location from said visual inspection device, wherein an insertion location substantially represents a reference to a point of entry where said tip of said visual inspection device is inserted into the opening of the physical asset;

receiving fiber information at the computing device captured and transmitted from said plurality of spatially sensitive fibers;

determining bending and motion information about said plurality of spatially sensitive fibers from said fiber information;

determining the real-time location of said tip of said visual inspection device using the insertion location and the bending and motion information;

identify the real-time location of said tip of said visual inspection device with respect to said engineering model data; and navigating said tip of said visual inspection device from a first location to a second location within the physical asset.

9. A method in accordance with claim 8, wherein said determining the location of the visual inspection device comprises:
 a first spatially sensitive fiber determining the vertical orientation of the visual inspection device; and
 a second spatially sensitive fiber to determining the horizontal orientation of the visual inspection device.

10. A method in accordance with claim 8, wherein said method further comprises compensating for error in the event of thermal drift effects within the plurality of spatially sensitive fibers using a supplemental spatially sensitive fiber.

11. A method in accordance with claim 8, wherein determining the location of the visual inspection device comprises:
 cascading the fiber information into a vector containing values at each length on the enclosure for shape and direction information associated with said plurality of spatially sensitive fibers; and
 determining the path of the visual inspection device using the vector and at least one algorithm.

12. A method in accordance with claim 8, wherein navigating the visual inspection device from a first location to a second location within the physical asset further comprises:
 receiving a second location from a computing device associated with the visual inspection device; and
 transmitting a navigation route to the computing device associated with the visual inspection device.

13. A method in accordance with claim 8, wherein the visual inspection device is a borescope.

14. A method in accordance with claim 8, wherein the plurality of spatially sensitive fibers comprise wavelength multiplexed fiber sensors for bending measurement at multiple locations.

15. A computer for enhanced tip-tracking and navigation of visual inspection devices, said computer comprises:
 a storage device including an engineering model data substantially representing a physical asset;
 a processor coupled to said storage device; and
 a memory device coupled to said processor and to said storage device, said memory device includes processor-executable instructions that, when executed by said processor, cause said computer to:
  receive an insertion location from said visual inspection device, wherein an insertion location substantially represents a reference to a point of entry where a tip of said visual inspection device is inserted into an opening of the physical asset;
  receive fiber information captured and transmitted from a plurality of spatially sensitive fibers;
  determine bending and motion information about said plurality of spatially sensitive fibers from said fiber information;
  determine the real-time location of the visual inspection device using the insertion location and the bending and motion information;
  identify the real-time location of the visual inspection device with respect to the engineering model data; and
  navigate the visual inspection device from a first location to a second location within the physical asset.

16. The computer of claim 15, wherein the processor-executable instructions that cause the computer to determine the location of the visual inspection device using the fiber information further cause the computer to:
 determine the vertical orientation of the visual inspection device using a first spatially sensitive fiber; and
 determine the horizontal orientation of the visual inspection device using a second spatially sensitive fiber.

17. The computer of claim 15, wherein the processor-executable instructions that cause the computer to receive fiber information associated with the visual inspection device from a plurality of spatially sensitive fibers further cause the computer to receive information from a supplemental spatially sensitive fiber to compensate for error in the event of thermal drift effects within the plurality of spatially sensitive fibers.

18. The computer of claim 15, wherein the processor-executable instructions that cause the computer to determine the location of the visual inspection device further cause the computer to:
 cascade the fiber information into a vector containing values at each length on the enclosure for shape and direction information associated with said plurality of spatially sensitive fibers; and
 determining, using said vector and at least one algorithm, the path of said visual inspection device.

19. The computer of claim 15, wherein the processor-executable instructions that cause the computer to navigate the visual inspection device from a first location to a second location within the physical asset further cause the computer to:
 receive a second location from a computing device associated with the visual inspection device; and
 transmit a navigation route to the computing device associated with the visual inspection device.

20. The computer of claim 15, wherein the at least two spatially sensitive fibers comprise wavelength multiplexed fiber sensors for bending measurement at multiple spots.

* * * * *